US008252542B2

(12) United States Patent
Roessler et al.

(10) Patent No.: US 8,252,542 B2
(45) Date of Patent: Aug. 28, 2012

(54) SERPIN B 13 AS A MARKER FOR SQUAMOUS CELL CARCINOMA OF THE LUNG

(75) Inventors: Markus Roessler, Germering (DE); Liliana Mantovani-Endl, Weilheim (DE); Michael Tacke, Munich (DE)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

(21) Appl. No.: 13/186,750

(22) Filed: Jul. 20, 2011

(65) Prior Publication Data

US 2011/0275100 A1    Nov. 10, 2011

Related U.S. Application Data

(63) Continuation of application No. PCT/EP2010/001270, filed on Mar. 2, 2010.

(30) Foreign Application Priority Data

Mar. 4, 2009 (EP) .................................... 09003092

(51) Int. Cl.
*G01N 33/53* (2006.01)
(52) U.S. Cl. ....................................................... 435/7.1
(58) Field of Classification Search .................. None
See application file for complete search history.

(56) References Cited

FOREIGN PATENT DOCUMENTS

| WO | 0151924 A3 | 7/2001 |
| WO | 0151928 A1 | 7/2001 |
| WO | 03015613 A3 | 7/2003 |
| WO | 2008151110 A3 | 12/2008 |

OTHER PUBLICATIONS

Tockman et al (Cancer Res., 1992, 52:2711s-2718s).*
Smith et al (Oncogene, 2003, 22: 8677-8687).*
Moussali et al (Experimental Dermatology, 2005, 14: 420-428).*
Mills et al (J Natl Cancer Inst, 1995, 87(14): Abstract).*
International Search Report issued Jun. 1, 2010 in PCT Application No. PCT/EP2010/001270.
International Preliminary Report on Patentability issued Feb. 23, 2011 in PCT Application PCT/EP2010/001270.
ABTS, Harry Frank et al., "Cloning and Characterization of Hurpin (Protease Inhibitor 13): A New Skin-specific, UV-repressible Serine Proteinase Inhibitor of the Ovalbumin Serpin Family," Journal of Molecular Biology, 1999, pp. 29-39, vol. 293.
Askew, David J. et al., "Comparative genomic analysis of the Glade B serpin cluster at human chromosome 18q21: amplification within the mouse squamous cell carcinoma antigen gene locus," Genomics, Jul. 1, 2004, pp. 176-184, vol. 84, No. 1.
Badola, Sunita et al., "Correlation of serpin-protease expression by comparative analysis of real-time PCR profiling data," Genomics, Aug. 1, 2006, pp. 173-184, vol. 88, No. 2.
Bylaite, M. et at, "Expression of cathepsin L and its inhibitor hurpin in inflammatory and neoplastic skin diseases," Experimental Dermatology, Feb. 2006, pp. 110-118, vol. 15, No. 2.
Jayakumar, Arumugam et al., "Inhibition of the cysteine proteinases cathepsins K and L by the serpin headpin (SERPINB13): a kinetic analysis," Archives of Biochemistry and Biophysics, 2003, pp. 367-374, vol. 409.
Moussali, H. et al., "Expression of hurpin, a serine proteinase inhibitor, in normal and pathological skin: overexpression and redistribution in psoriasis and cutaneous carcinomas," Experimental Dermatology, 2005, pp. 429-428, vol. 14.
Smith, Shirley L. et al., "Maspin—the most commonly-expressed gene of the 18q21.3 serpin cluster in lung cancer—is strongly expressed in preneoplastic bronchial lesions," Oncogene, Nov. 27, 2003, pp. 8677-8687, vol. 22, No. 54.
Spring, Paul et al., "Identification and cDNA Cloning of headpin, a Novel Differentially Expressed Serpin That Maps to Chromosome 18q," Biochemical and Biophysical Research Communications, 1999, pp. 299-304, vol. 264.
Walz, Markus et al., "Expression of the human Cathepsin L inhibitor hurpin in mice: skin alterations and increased carcinogenesis," Experimental Dermatology, 2007, pp. 715-723, vol. 16.
Welss, Thomas et al., "Hurpin is a Selective Inhibitor of Lysosomal Cathepsin L and Protects Keratinocytes from Ultraviolet-Induced Apoptosis," Biochemistry, 2003, pp. 7381-7389, vol. 42.

* cited by examiner

*Primary Examiner* — Sean Aeder

(57) ABSTRACT

Disclosed is a method aiding in the assessment of squamous cell carcinoma (SCC). It involves the use of the protein serpin B13 as a marker of SCC. Furthermore, the disclosure relates to a method for assessing lung cancer in a tissue sample derived from a patient having non-small cell lung carcinoma (NSCLC) and for differentiating SCC from adenocarcinoma or large cell carcinoma of the lung.

31 Claims, 2 Drawing Sheets

SERPIN B 13 AS A MARKER FOR SQUAMOUS CELL CARCINOMA OF THE LUNG

RELATED APPLICATIONS

This application is a continuation of PCT/EP2010/001270 filed Mar. 2, 2010 and claims priority to EP 09003092.5 filed Mar. 4, 2009.

SEQUENCE LISTING

The instant application contains a Sequence Listing which has been submitted in ASCII format via EFS-Web and is hereby incorporated by reference in its entirety. Said ASCII copy, created on Jul. 18, 2011, is named 25424US.txt, and is 7,502 bytes in size.

FIELD OF THE INVENTION

The present invention relates to a method aiding in the assessment of squamous cell carcinoma (SCC). It discloses the use of the protein serpin B13 as a marker of SCC. Furthermore, it relates to a method for assessing lung cancer in a tissue sample derived from a patient having non-small cell lung carcinoma (NSCLC) and for differentiating SCC from adenocarcinoma or large cell carcinoma of the lung.

BACKGROUND

Cancer remains a major public health challenge despite progress in detection and therapy. Amongst the various types of cancer, LC is a frequent cancer in the Western world and among the most frequent causes of cancer-related mortality. It is the most common cause of cancer-related deaths among both men and women in the USA. It is predominantly a disease of the elderly: incidence increases with age, reaching 482/100,000 men>65 years, and peaks at age 75, reaching about 502/100,000 men. A man aged 65 has a 50 times greater risk of developing lung cancer than a man aged 25, and a 3 to 4 times greater risk than men aged 45 to 64.

About 90% of lung cancer cases in men and 80% in women are attributable to cigarette smoking. The risk of lung cancer is related to the total years of smoking, which exposes smokers to carcinogens and promoting agents. Risk also increases in the elderly because of the age-related decline in cellular DNA repair. From initial exposure to cigarette smoke to clinical presentation, lung cancer probably has a 15- to 20-year natural history.

The majority of LC tumors can be divided into small cell lung carcinoma (SCLC) and non-small cell lung carcinoma (NSCLC), which again is grouped into three major histological tumor types, i.e., squamous cell carcinoma, adenocarcinoma and large cell carcinoma.

SCLC accounts for about 20-25% of all lung cancer cases. SCLC is an aggressive neuroendocrine type of LC and has a very poor prognosis even if detected in early stages. SCLC is rarely amenable to curative treatment by resection. Because of the speed with which the disease progresses, SCLC is generally categorized using only two stages, i.e., limited and extensive disease, rather than the more complex TNM staging system (see below).

About 75-80% of LC cases are grouped into the class of NSCLC including squamous cell carcinoma (carcinoma=CA), adeno CA (comprising the subclasses of acinar CA, papillary CA, bronchoalveolar tumor, solid tumor, and mixed subtypes), and large cell carcinoma (comprising the subclasses of giant cell tumors, clear cell CA, adenosquamous CA, and undifferentiated CA).

NSCLC, if detected at late stages, has a very poor prognosis. The staging of cancer is the classification of the disease in terms of extent, progression, cell type and tumor grade. It groups cancer patients so that generalizations can be made about prognosis and the choice of therapy.

Today, the TNM system is the most widely used classification system based on the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer) (Sobin, L. H. and Fleming, I. D., TNM Classification of Malignant Tumors, Fifth Edition (1997), pp. 1803-1804.

Surgical resection of the primary tumor is widely accepted as the treatment of choice for early stage NSCLC. With the progression of NSCLC and, more specifically, the transition from stage IIIa (T3N1M0, T1N2M0, T2N2M0, T3N2M0) to IIIb (T4N0M0, T4N1M0, T4N2M0), a significant shift in the physician's approach is precipitated. However, if the cancer is detected during the more early stages (Ia-IIIa; preferably up to stage T3N1M0), the five-year survival rate varies between 35% and 80%. Detection at stage Ia ((T1N0M0); small tumor size, no metastasis) has evidently the best prognosis with a five-year survival of up to 80%.

Surgery is rarely, if ever, used in the management of stage IIIb-IV of NSCLC. Stage IV corresponds to distant metastasis, i.e., spread of the disease beyond the lungs and regional lymph nodes. The five-year survival rate in the later stages III and IV drops to between less than 15% and 1%, respectively.

What is especially important is that early diagnosis of NSCLC translates to a much better prognosis. Patients diagnosed as early as in stage Ia (T1N0M0), Ib (T2N0M0), IIa (T1N1M0), IIb, (T3N0M0), and IIIa (T3N1M0), if treated properly have an up to 80% chance of survival 5 years after diagnosis. This has to be compared to a 5-years survival rate of less than 1% for patients diagnosed once distant metastases are already present.

The earlier LC is diagnosed the better the chances of long term survival.

As mentioned above, the pathologist groups lung cancer into four major histological patterns, i.e., squamous cell carcinoma, adenocarcinoma, large cell carcinoma (altogether=NSCLC), and small cell carcinoma. However, what is quite important to note: often, two or more of these patterns occur simultaneously and histological grouping is extremely dependent on the skills of the pathologist in charge.

Additional means that could help in a more reproducible grouping of various types of lung cancer are urgently needed. Especially a marker indicative for SCC within the group of NSCLC tumors would be represent an important tool to aid such diagnosis.

It has surprisingly been found that the marker serpin B 13 represents an excellent tool to assess lung cancer. Using the marker serpin B 13 it is for example possible to differentiate squamous cell carcinoma from other histological types of lung cancer, e.g., adenocarcinoma.

SUMMARY OF THE INVENTION

In one embodiment the present invention relates to a method for assessing squamous cell carcinoma (SCC) of the lung in vitro comprising (a) measuring serpin B 13 in a test sample and (b) using the measurement result of step (a) in the assessment of squamous cell carcinoma of the lung, wherein a positive measurement result for serpin B 13 is indicative for squamous cell carcinoma of the lung.

Further a method for assessing squamous cell carcinoma of the lung in vitro comprising (a) measuring serpin B 13 in a test sample, (b) measuring serpin B 13 in a control sample and (c) comparing the measurement result of steps (a) and (b) in the assessment of squamous cell carcinoma of the lung, wherein an elevated level of serpin B in said test sample as compared to the level in the control sample is indicative for squamous cell carcinoma of the lung is described.

The present invention further discloses a method for differential diagnosis of a squamous cell carcinoma of the lung as compared to other non-small cell lung carcinoma (NSCLC) in vitro comprising (a) measuring serpin B 13 in a test sample comprising non-small cell lung carcinoma cells and (b) using the measurement result of step (a) in the for differential diagnosis of a squamous cell carcinoma as compared to other NSCLC, wherein a positive measurement result for serpin B 13 is indicative for squamous cell carcinoma of the lung and a negative measurement result for serpin B 13 is indicative for other NSCLC.

The present invention also relates to the use of the marker serpin B 13 in the assessment of squamous cell carcinoma of the lung and for differentiating squamous cell carcinoma of the lung from other types of NSCLC, like adenocarcinoma of the lung.

DESCRIPTION OF THE SEQUENCE LISTING

Figure 1:
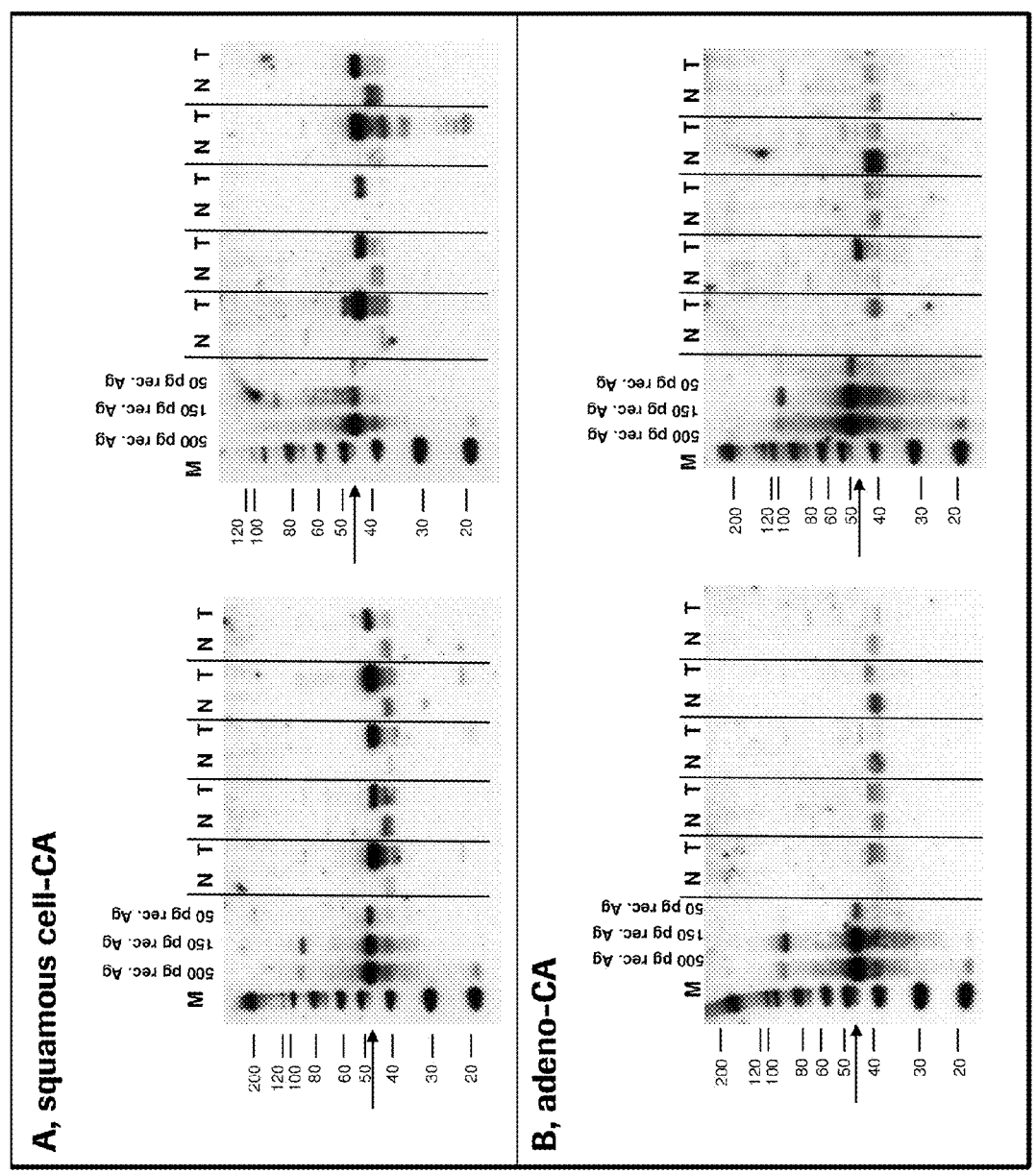
FIG. 1 shows the western blot results (immunostaining for serpin B 13) for 10 patients with SCC and 10 patients with Adeno-Ca, respectively. Obviously, signal intensity for serpin B 13 was increased in the tumor tissue lysates in all 10 patients classified as SCC, while in Adeno-Ca the serpin B 13 protein was merely detectable in 1 patient or not present at all.

SEQ ID NO: 1 shows the amino acid sequence of the serpin B 13 protein (44.3 kDa; 391 amino acids; SWISS-PROT Acc. No.: Q9UIV8)
SEQ ID NO: 2 shows the amino acid sequence of a serpin B 13 protein isoform (38.4 kDa, 339 amino acids) produced by alternative splicing
SEQ ID NO: 3 forward primer LC5for-EcoRI (features for the EcoRI cloning site, the ribosomal binding site and an N-terminal peptide extension, which is shown in SEQ ID NO: 5)
SEQ ID NO: 4 reverse primer LC5rev-HindIII
SEQ ID NO: 5 N-terminal peptide extension

DETAILED DESCRIPTION OF THE INVENTION

In a preferred embodiment the present invention relates to a method for assessing squamous cell carcinoma of the lung in vitro comprising (a) measuring serpin B 13 in a test sample and (b) using the measurement result of step (a) in the assessment of squamous cell carcinoma of the lung, wherein a positive measurement result for serpin B 13 is indicative for squamous cell carcinoma of the lung.

The terms "measuring" or "measurement" relate to a qualitative or a quantitative measurement of serpin B 13 in a sample. In a preferred embodiment the measurement is a qualitative or semi-quantitative measurement, i.e., it is determined whether serpin B 13 is present or absent or it is determined whether the concentration of serpin B 13 is above or below a cut-off value. As the skilled artisan will appreciate, in a Yes—(presence) or No—(absence) assay, the assay sensitivity is usually set to match the cut-off value. A cut-off value can for example be determined from the testing of a group of healthy individuals. Preferably the cut-off is set to result in a specificity of 90%, also preferred the cut-off is set to result in a specificity of 95%, or also preferred the cut-off is set to result in a specificity of 98%. Presence of a value above the cut-off value can for example be indicative for the presence of squamous cell carcinoma of the lung. A measurement result is classified as positive, if the value determined is above the cut-off value.

The serpin B 13 protein (proteinase inhibitor 13, HaCaT UV-repressible serpin, hurpin, headpin; serpin B 13; SWISS-PROT Acc.No.: Q9UIV8) is a 44.3 kDa protein and consists of 391 amino acids, characterized by SEQ ID NO: 1. One isoform (38.4 kDa, 339 aa) which is produced by alternative splicing is reported in the literature (SEQ ID NO: 2). Serpin13 belongs to the broadly distributed protein superfamily of serpins (serine protease inhibitors). Generally, serpins are protease inhibitors that use a conformational change to inhibit target enzymes, mainly serine proteases. In particular, serpin B 13 was reported to inhibit cathepsin K and L, respectively (Welss, T. et al., Biochemistry 42 (2003) 7381-7389; Jayakumar, A. et al., Arch. Biochem. Biophys. 409 (2003) 367-374).

Serpin13 was originally discovered as an UV-repressible gene in HaCaT cells (Abts, H. F. et al., J. Mol. Biol. 293 (1999) 29-39). Independently, it was described as "headpin" and the corresponding gene was mapped on chromosome 18q by other authors (Spring, P. et al., Biochem. Biophys. Res. Comm. 264 (1999) 299-304). In this study, northern blot analyses and relative RT-PCR revealed that serpin B 13 mRNA expression is downregulated in oral cavity squamous cell carcinomas as compared to normal squamous epithelium.

Early studies based on RT-PCR analyses revealed an overexpression of serpin B 13 in affected skin of patients suffering from psoriasis as compared to unaffected skin (Abts, H. F. et al., J. Mol. Biol. 293 (1999) 29-39). These findings were confirmed on the protein level by western blotting an IHC in more recent studies. In normal skin, serpin B 13 was mainly expressed in the stratum basale (Moussali, H. et al., Exp. Dermatol. 14 (2005) 420-428). The distribution and expression level of serpin B 13 is different in psoriatic skin; highest expression is found in the stratum granulosum. In the same study the authors report overexpression of Serpin B 13 in Lupus erythematosus and malignant tumors of the skin. Again, the authors corroborated their findings with RT-PCR. The correlation of the expression of serpin B 13 and its target protease Cat L was analyzed in another study (Bylaite, M. et al., Exp. Dermatol. 15 (2006) 110-118). The authors show again that serpin B 13 expression is enhanced and redistributed in malignant tumors of the skin as compared to normal tissue; however there was no direct correlation in the expression of serpin B 13 and Cat L.

Recently, Walz, M. et al. (Exp. Dermatol. 16 (2007) 715-723) generated transgenic mice expressing human serpin B 13 in addition to endogenous murine Serpin B 13. These transgenic mice were characterized by abnormal abdominal fur and higher susceptibility to skin cancer after chemical carcinogenesis. These findings suggest an important role of serpin B 13 in the development of skin diseases.

As obvious to the skilled artisan, the present invention shall not be construed to be limited to the full-length protein serpin B 13 of SEQ ID NO: 1. Physiological or artificial fragments of serpin B 13, secondary modifications of serpin B 13, as well as allelic variants of serpin B 13 are also encompassed by the present invention. Variants of a polypeptide are encoded by the same gene, but may differ in their isoelectric point (PI) or molecular weight (MW), or both, e.g., as a result of alternative mRNA or pre-mRNA processing. The amino acid sequence of a variant is to 95% or more identical to the corresponding marker sequence. Artificial fragments preferably encompass a peptide produced synthetically or by recombinant techniques, which at least comprises one epitope of diagnostic interest consisting of at least 6, 7, 8, 9 or 10 contiguous amino acids as derived from the sequence disclosed in SEQ ID NO: 1. Such fragment may advantageously be used for generation of antibodies or as a standard in an immunoassay.

As used herein, each of the following terms has the meaning associated with it in this section.

The articles "a" and "an" are used herein to refer to one or to more than one (i.e., to at least one) of the grammatical object of the article. By way of example, "a marker" means one marker or more than one marker. The term "at least" is used to indicate that optionally one or more further objects may be present.

The expression "one or more" denotes 1 to 50, preferably 1 to 20 also preferred 2, 3, 4, 5, 6, 7, 8, 9, 10, 12, or 15.

The term "marker" or "biochemical marker" as used herein refers to a molecule to be used as a target for analyzing a patient's test sample. In one embodiment examples of such molecular targets are proteins or polypeptides. Proteins or polypeptides used as a marker in the present invention are contemplated to include naturally occurring variants of said protein as well as fragments of said protein or said variant, in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. In addition, or in the alternative a marker polypeptide or a variant thereof may carry a post-translational modification. Preferred posttranslational modifications are glycosylation, acylation, and/or phosphorylation.

Preferably the marker serpin B 13 is specifically measured from a sample by use of a specific binding agent.

A specific binding agent is, e.g., a receptor for serpin B 13, a lectin binding to serpin B 13 or an antibody to serpin B 13. Preferably a specific binding agent is used that binds to both isoforms of serpin B 13. A specific binding agent has at least an affinity of $10^7$ l/mol for its corresponding target molecule. The specific binding agent preferably has an affinity of $10^8$ l/mol or also preferred of $10^9$ l/mol for its target molecule. As the skilled artisan will appreciate the term specific is used to indicate that other biomolecules present in the sample do not significantly bind to the binding agent specific for serpin B 13. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfil both the above minimum criteria for affinity as well as for specificity.

A specific binding agent preferably is an antibody reactive with serpin B 13. The term antibody refers to a polyclonal antibody, a monoclonal antibody, antigen binding fragments of such antibodies, single chain antibodies as well as to genetic constructs comprising the binding domain of an antibody.

Any antibody fragment retaining the above criteria of a specific binding agent can be used. Antibodies are generated by state of the art procedures, e.g., as described in Tijssen (Tijssen, P., Practice and theory of enzyme immunoassays, 11, Elsevier Science Publishers B.V., Amsterdam, the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention polyclonal antibodies raised in rabbits may be used. However, clearly also polyclonal antibodies from different species, e.g., rats or guinea pigs, as well as monoclonal antibodies can also be used. Since monoclonal antibodies can be produced in any amount required with constant properties, they represent ideal tools in development of an assay for clinical routine. The generation and the use of monoclonal antibodies to serpin B13 and their use in a method according to the present invention, respectively, represent yet other preferred embodiments.

The term "test sample" as used herein refers to a biological sample obtained from an individual for the purpose of evaluation in vitro.

The term "assessing squamous carcinoma of the lung" is used to indicate that the method according to the present invention will (alone or together with other markers or variables, e.g., the criteria set forth by the UICC (see above)), e.g., aid the physician to establish or confirm the absence or presence of SCC.

As the skilled artisan will appreciate, any such assessment is made in vitro. The patient sample is discarded afterwards. The patient sample is solely used for the in vitro diagnostic method of the invention and the material of the patient sample is not transferred back into the patient's body. Typically, the sample is a sample comprising cells.

It will be recognized by those with skill in the immunohistochemistry arts that dye lot variations and variability in certain environmental conditions, such as relative humidity can affect results obtained at different times using the methods of the invention. In certain embodiments of the methods of the present invention, reagent and lot to lot variability is controlled by using the same reagents to stain the test sample cells and appropriate control sample cells.

In a preferred embodiment the present invention relates to a method for assessing SCC in vitro comprising measuring serpin B 13 in a single test sample the and using the measurement result in the assessment of SCC. In some circumstances it may be helpful to also provide a control sample in addition to the test sample obtained from the patient. Such control sample can be a negative control sample, a positive control sample or mixed control comprising one or more of these types of controls. A negative control sample preferably will comprise normal lung tissue, lung cancers of various subtypes like, small cell carcinoma of the lung, non-small cell lung carcinoma, adenocarcinoma of the lung, large cell carcinoma of the lung, or various combinations thereof. A positive control sample preferably will comprise tissue classified as squamous cell carcinoma of the lung.

In a preferred embodiment the present invention discloses a method for assessing squamous cell carcinoma of the lung in vitro comprising (a) measuring serpin B 13 in a test sample, (b) measuring serpin B 13 in a negative control sample and (c) comparing the measurement result of steps (a) and (b) in the assessment of squamous cell carcinoma of the lung, wherein an elevated level of serpin B in said test sample as compared to the level in the negative control sample is indicative for squamous cell carcinoma of the lung.

As indicated above a sample comprising squamous cell carcinoma of the lung in certain settings might be used as a positive control and preferably assayed in parallel with the sample to be investigated. In such setting a positive result for serpin B 13 in the positive control sample indicates that the testing procedure has worked on the technical level. Positive staining of the test sample for serpin B13 under these conditions a test sample indicates that the underlying malignancy is SCC.

The inventors of the present invention have surprisingly been able to demonstrate that the marker protein serpin B 13 shows a strong association with squamous cell carcinoma of the lung Taking into account the uncertainties of classifying the various types of lung cancer, and especially of SCC, it may well be that staining for serpin B 13 may become one of the pivotal criteria in the assessment of patients with NSCLC and their grouping into SCC and other "non-SCC" lung cancer.

The ideal scenario for assessing a certain clinical (disease) entity would be a situation wherein a single event or process would cause the respective disease as, e.g., in most infectious diseases. In all other cases correct diagnosis can be very difficult, especially when the etiology of the disease is not fully understood as is the case for LC. As the skilled artisan will appreciate, no biochemical marker is diagnostic with 100% specificity and at the same time 100% sensitivity for a given multifactorial disease, as for example for LC. Rather, biochemical markers, e.g., CYFRA 21-1, CEA, NSE, pro-GRP, or as shown here, serpin B 13 can be used to assess with a certain likelihood or predictive value, e.g., the presence, absence, or the severity of a disease. Therefore in routine clinical diagnosis, generally various clinical symptoms and biological markers are considered together in the assessment of an underlying disease.

The skilled pathologist can easily group lung cancer into the two major categories of small cell lung carcinoma and non-small cell lung carcinoma. It is, however, difficult to further narrow down the tumor sub-types, especially for a patient initially found as having NSCLC. As mentioned above, NSCLC is understood to comprise the three major disease subgroups: squamous cell carcinoma, adeno CA, and large cell carcinoma. A diagnostic means helpful in differentiating squamous cell carcinoma from all other types of NSCLC (i.e., NSCLC that is not SCC) is disclosed in the present invention.

In a further embodiment the present invention discloses a method for differential diagnosis of a squamous cell carcinoma as compared to other types of NSCLC in vitro comprising (a) measuring serpin B 13 in a test sample comprising non-small cell lung carcinoma cells and (b) using the measurement result of step (a) in the for differential diagnosis of a squamous cell carcinoma as compared to other NSCLC, wherein a positive measurement result for serpin B 13 is indicative for squamous cell carcinoma of the lung and a negative measurement result for serpin B 13 is indicative for other types of NSCLC.

In the methods of the present invention, the test sample or patient sample preferably is a sample comprising cells, e.g., a tissue sample.

Preferably the test sample is a piece of tissue as obtained by biopsy or surgery. It is also preferred that such test sample is a tissue section.

Alternatively cells may be derived from the lung by obtaining bronchoalveolar lavage, they may be aspired by devices appropriate to collect epithelial lining fluid (comprising cells), or cells may be obtained from sputum. In a preferred embodiment the present invention and the various methods disclosed herein, therefore relate to a test sample comprising cells that are derived from bronchoalveolar lavage or epithelial lining fluid.

A test sample comprising cells can be subjected to various routes of analysis. In one preferred embodiment serpin B 13 will be measured in situ, i.e., within the cells or tissue of the test sample in another preferred embodiment the cells of a test sample may be solubilized and the serpin B13 measured in the cell or tissue lysate.

For measurement of serpin B 13 in situ it is preferred that the test sample comprising the cells to be investigated is mounted on a microscope slide. In one embodiment such sample may be a sample that is not fixed with formaldehyde and not embedded, e.g., not embedded in paraffin, e.g., a sample known to the skilled artisan as fresh tissue sample or as a fresh frozen tissue sample, respectively.

In clinical routine it is, however, preferred that a sample comprising cells is subjected to a standardized fixation and/or embedding procedure. In a preferred mode the methods according to present invention will be carried out based on a test sample that has been formalin fixed and paraffin embedded. It is obvious to the skilled artisan that a sample that had previously been fixed and embedded has to be pre-treated in order to at least remove the embedding material. If furthermore required, in the art of immunohistochemistry a variety of methods is at stake that can be used in order regain, e.g., immunologically detectable epitopes. Such methods are collectively known to the skilled artisan as methods of antigen retrieval.

A method according to the present invention should certainly be used if a test sample has to be investigated that might contain or is suspected to contain neoplastic cells of the lung. In a preferred embodiment the present invention will be practiced with a test sample that is suspected to contain neoplastic cells.

Whenever serpin B 13 is to be measured in situ (on or inside a cell, in a tissue section or the like) the method used in such measurement will preferably be any appropriate procedure of immunohistochemistry. In a preferred embodiment serpin B 13 is measured by an immunostaining method.

A cancer diagnosis, both initial diagnosis of disease and subsequent monitoring of the disease course, before, during, or after treatment, is conventionally confirmed through histological examination of cell or tissue samples removed from a patient. Clinical pathologists need to be able to accurately determine whether such samples are benign or malignant and to classify the aggressiveness of tumor samples deemed to be malignant, because these determinations often form the basis for selecting a suitable course of patient treatment. Similarly, the pathologist needs to be able to detect the extent to which a cancer has grown or gone into remission, particularly as a result of or consequent to treatment, most particularly treatment with chemotherapeutic or biological agents.

Histological examination traditionally entails tissue-staining procedures that permit morphological features of a sample to be readily observed under a light microscope. A pathologist, after examining the stained sample, typically makes a qualitative determination of whether the tumor sample is malignant. It is difficult, however, to ascertain a tumor's aggressiveness merely through histological examination of the sample, because a tumor's aggressiveness is often a result of the biochemistry of the cells within the tumor, such as protein expression or suppression and protein activation, which may or may not be reflected by the morphology of the sample. Therefore, it is important to be able to assess the biochemistry of the cells within a tumor sample. Further, it is desirable to be able to observe and quantify both tumor related genes or proteins, respectively.

In the practice of the methods of this invention serpin B 13 can be detected using a specific reagent, most preferably an antibody, that is itself detectably labeled, or using an unlabeled, serpin B 13-specific antibody and a second antibody that is detectably labeled and recognizes the serpin B 13-specific antibody. Stained cells or tissue samples usually are evaluated under the microscope by a skilled pathologist.

In a preferred embodiment of the methods of the present invention, a two-component immunohistochemical staining system is used to differentially stain serpin B 13 and the tissue or cell sample so that the stained serpin B 13 can be more readily distinguished from the counterstained tissue or cell sample. Following immunohistochemical staining, the optical image of the tissue or cell sample preferably generated by a computer-aided image analysis system is then magnified under a light microscope and separated into a pair of images. The separated images are enhanced using a pair of optical filters, one having a maximum absorption corresponding to the stain and the other having a maximum absorption corresponding to the counterstain, thereby providing an optimum discrimination between the two stains. Automated (computer-aided) image analysis systems known in the art can augment visual examination of samples. In a representative system, the cell or tissue sample is exposed to detectably labeled reagents specific for a particular biological marker, and the magnified image of the cell is then processed by a computer that receives the image from a charge-coupled device (CCD) or camera such as a television camera. Such a system can be used to detect and measure the level of serpin B 13 in a sample. This methodology provides more accurate diagnosis of cancer and a better characterization of gene expression in histologically identified cancer cells.

A description of exemplary procedures for quantitative immunohistochemical image analysis of tissue samples can be found, generally, in WO 01/51924 and WO 01/51928 both of which are incorporated herein by reference in their entirety. As an example, Quantitative image analysis can be performed on a Cell Analysis Systems Model 200, available from Becton Dickinson Company, Mountain View, Calif. Quantitative image analysis, as encompassed by this invention, can be performed on systems from other vendors, such as, but not limited to, ChromaVision Medical Systems (San Juan Capistrano, Calif.).

In certain embodiments, the inventive methods are practiced using such an image analysis system as follows. After immunohistochemical staining as described above, a quantified measure of the percentage of expressing cells can be taken by digitizing microscope images of stained samples, and converting light intensity values in each picture element (pixel) of the digitized image to optical density values, which correspond to the percentage of stained cell components (such as nuclei). More specifically, computerized image analysis can be used to determine a quantity of cells having a particular stain using a digital grey scale image. Grey scale images are representative of the amount of an optical enhancement factor, such as a chromogen, which binds to a specific target under study and thereby allows optical amplification and visualization of the target.

In a first step, any expressed target protein in the cells is identified by adding a detectably-labeled primary antibody specific for the target protein, or alternatively an unlabeled primary antibody and a detectably-labeled secondary antibody specific for the primary antibody. The antibodies are incubated with the sample for a time to form complexes if these antigens are present. The complexes are then visualized, either by directly detecting the label, or, if the detectable label is an enzyme, incubating the sections with a compound, such as a chromogen under appropriate conditions. As an example, the primary antibody can be labeled peroxidase, with the subsequent use of the chromogen DAB. In a second step, the tissue is counterstained with another optical enhancement factor, such as, but not limited to ethyl green. Although a staining technique using peroxidase and ethyl green is exemplary, other stains and optical enhancement factors are also suitable. For example, other chromogens can be used with peroxidase, including, but not limited to 3-Amino-9-Ethyl-carbazole (AEC), which produces a red color, and 4-Chloro-1-Naphthol. In addition, other enzymes that can be used to label the primary antibody are encompassed by this invention, including, but not limited alkaline phosphatase. Examples of chromogens that can be used with alkaline phosphatase include, but are not limited to Fast Red, Fast Green, and 5-bromo-4-chloro-3-indolyl phosphate/nitroblue tetrazolium (BCIP/NBT). In addition, the use of florescent dyes is encompassed by methods of the present invention. Non-limiting examples of florescent dyes are Fluorescein (fluorescein isothiocyanate or FITC) and Rhodamine.

Further, the use of ethyl green is exemplary of counter stains, but other counter stains may be used in a method of the present invention. For example, a non-limiting list of additional counter stains includes Hematoxylin, fast red, methyl green. A counter stain is chosen for a particular stain based on the spectral separation that can be achieved such that filtering at two separate wavelengths can be achieved. For example, ethyl green offers good spectral separation from the DAB precipitate, as described in more detail below. Other examples of pairs of stains/counter stains that offer good spectral separation include, but are not limited to, Fast Red and Hematoxylin, AEC and Hematoxylin, and FITC and Texas Red.

Those skilled in the art will recognize that this list of stains and counter-stain is merely exemplary and, therefore, does not serve to limit the invention.

As mentioned above, serpin B 13 can also be measured from a test sample wherein cells have been solubilized or treated otherwise to release serpin B 13. In a preferred embodiment a test sample is treated to release serpin B 13 and serpin B 13 is measured by an immunoassay procedure. Preferred immunoassay methods by which serpin B 13 can be measured in a solubilized sample are enzyme linked immunosorbent assay (ELISA), chemiluminescence based immuno assay (e.g., ELECSYS from Roche) or western blot.

The use of the marker serpin B 13 in the assessment of squamous cell carcinoma of the lung represents a further preferred embodiment according to the present invention.

It is also preferred to use of the marker serpin B 13 to differentiate squamous cell carcinoma of the lung from other types of non-small cell carcinoma of the lung in a tissue sample from a patient previously classified as having non-small cell lung carcinoma.

The following examples, sequence listing and figures are provided to aid the understanding of the present invention, the true scope of which is set forth in the appended claims. It is understood that modifications can be made in the procedures set forth without departing from the spirit of the invention.

EXAMPLE 1

Generation of Antibodies to Serpin B 13

Polyclonal antibody to Serpin B 13 is generated for further use of the antibody in immunodetection assays, e.g., western blotting and IHC.

a) Recombinant Protein Expression in E. coli:

In order to generate antibodies against serpin B 13, the recombinant antigen is produced in E. coli. Therefore, the serpin B 13 coding region is PCR amplified from the full-length cDNA clone DKFZp686E1318Q2 obtained from the German Resource Center for Genome Research (RZPD, Berlin, Germany) using the forward primer LC5 for EcoRI, 5'ATGCGAATTCATTAAAGAGGAGAAATTAACTATG-AGAGG<u>ATCGCAT</u>CACCATCACCATCACATTGA<u>AG</u>-GCCGTGATTCACTTGGCGCCGTCAGCACTC (SEQ ID NO: 3) (EcoRI site and start codon underlined), and reverse primer LC5rev-HindIII, 5'GCATAAGCTTTCATTAA-GGAGAAGAAAATCTGCCGA<u>AGAAG</u> (SEQ ID NO: 4) (HindIII site underlined).

The forward primer features (besides the EcoRI cloning and ribosomal binding sites) oligonucleotides coding for an N-terminal MRGSHHHHHHIEGR (SEQ ID NO: 5) peptide extension introduced in-frame to the serpin B 13 polypeptide. The EcoRI/HindIII digested PCR fragment is ligated into the corresponding pQE-30 (Qiagen, Hilden, Germany) vector fragment which is subsequently transformed into E. coli XL1-blue competent cells. After sequence analysis, the plasmid is transformed into E. coli BL21 competent cells for expression under the IPTG-inducible T5 promoter of the pQE vector series following the manufacturer's instructions.

For purification of the MRGSHHHHHHIEGR-serpin (SEQ ID NO: 5) B 13 fusion protein, 1 l of an over-night induced bacterial culture is pelleted by centrifugation and the cell pellet is lysed by resuspension in 100 mM sodium-phosphate buffer, pH 8.0, 7 M guanidium-hydrochloride, 5 mM imidazole, 20 mM thioglycerole. Insoluble material is pelleted by centrifugation and the supernatant is applied to Ni-nitrilotriacetic acid (Ni-NTA) metal-affinity chromatography: The column is washed with several bed volumes of lysis buffer followed by washes with a) 100 mM sodium-phosphate buffer, pH 8.0, 10 mM Tris-HCl, pH 8.0, 8 M urea, 20 mM thioglycerole; b) 100 mM sodium-phosphate buffer, pH 8.0, 0.5% sodium-dodecylsulfate (SDS), 20 mM thioglycerole; and c) 100 mM sodium-phosphate buffer, pH 8.0, 0.1% SDS, 20 mM thioglycerole. Finally, bound antigen is eluted using 100 mM sodium-phosphate buffer, pH 5.0, 0.1% SDS, 20 mM thioglycerole, under acid conditions, and stored in the same buffer at 4° C.

b) Generation of Polyclonal Antibodies:
Immunization:

For immunization, a fresh emulsion of the protein solution (100 μg/ml protein serpin B 13) and complete Freund's adjuvant at the ratio of 1:1 is prepared. Each rabbit is immunized with 1 ml of the emulsion at days 1, 7, 14 and 30, 60 and 90. Blood is drawn and resulting anti-serpin B 13 serum used for further experiments as described in Examples 2 and 3.

EXAMPLE 2

Western Blotting for the Detection of Serpin B 13 in Human Lung Cancer Tissue Using a Polyclonal Antibody Described in Example 1

Tissue Preparation:

0.8-1.2 g of frozen tissue are cut into small pieces, transferred to the chilled grinding jar of a mixer ball mill and completely frozen by liquid nitrogen. The tissue is pulverized in the ball mill, dissolved in the 10-fold volume (w/v) of lysis buffer (40 mM Na-citrate, 5 mM $MgCl_2$, 1% Genapol X-080, 0.02% Na-azide, Complete EDTA-free [Roche Diagnostics GmbH, Mannheim, Germany, Cat. No. 1 873 580]) and subsequently homogenized in a Wheaton glass homogenizer (20× loose fitting, 20× tight fitting). The homogenate is subjected to centrifugation (10' at 5,000×g), the supernatant is transferred to another vial and again subjected to centrifugation (15' at 20,000×g). The resulting supernatant contains the soluble proteins and is used for further analysis.

SDS-PAGE and western-blotting are carried out using reagents and equipment of Invitrogen, Karlsruhe, Germany. For each tissue sample tested, 15 μg of tissue lysate are diluted in reducing NuPAGE (Invitrogen) SDS sample buffer and heated for 10 min at 95° C. Samples are run on 4-12% NuPAGE gels (Tris-Glycine) in the MES running buffer system. The gel-separated protein mixture is blotted onto nitrocellulose membranes using the Invitrogen XCell II™ Blot Module (Invitrogen) and the NuPAGE® transfer buffer system. The membranes are washed 3 times in PBS/0.05% TWEEN 20 and blocked with Roti-Block blocking buffer (A151.1; Carl Roth GmbH, Karlsruhe, Germany) for 2 h. The primary antibody, polyclonal rabbit anti-serpin B 13 serum (generation described in Example 2), is diluted 1:30,000 in Roti-Block blocking buffer and incubated with the membrane for 1 h. The membranes are washed 6 times in PBS/0.05% TWEEN 20. The specifically bound primary rabbit antibody is labeled with a POD-conjugated polyclonal sheep anti-rabbit IgG antibody, diluted to 10 mU/ml in 0.5× Roti-Block blocking buffer. After incubation for 1 h, the membranes are washed 6 times in PBS/0.05% TWEEN 20. For detection of the bound POD-conjugated anti-rabbit antibody, the membrane is incubated with the Lumi-Light$^{PLus}$ Western Blotting Substrate (Order-No. 2015196, Roche Diagnostics GmbH, Mannheim, Germany) and exposed to an autoradiographic film.

10 patients with SCC and 10 patients with Adeno-Ca, respectively, were analyzed with WB (FIG. 1). Obviously, signal intensity for serpin B 13 was increased in the tumor tissue lysates in all 10 patients, while in Adeno-Ca serpin B 13 expression was merely detectable in 1 patient at all. Thus, SCC specific overexpression of serpin B 13 in tumor tissue is clearly shown by western blotting analyses.

EXAMPLE 3

Immunohistochemistry (IHC) Analyses for the Detection of Serpin B 13 in Human Lung Cancer Tissue Using a Polyclonal Antibody Described in Example 1

Paraffin-embedded tissues were cut into 2 μm serial sections, deparaffinized in xylene (3×5 min) and rehydrated through a series of graded ethanol followed by two washing steps with deionized water and PBS (1×2 min). Antigen retrieval was performed with Retrivit pH 4.0 (Innogenex) for 20 min at 97° C.-100° C. Slides were let cool down for 20 min and rinsed with PBS (2×1 min). Endogenous peroxidase activity was blocked by incubation in 3% H2O2 in PBS for 5 min, the slides were then rinsed twice with PBS followed by TBS+TWEEN 20 (LabVision 1666789) once for 3 min. Blocking of immunoglobulin unspecific binding was performed with horse serum 1% in PBS (Horse-Blocking Serum, Vectastain ABC kit, Elite Universal, Vector PK6200) for 20 min at room temperature. Endogenous biotin was blocked with Biotin Blocking System (Dako X0590) following the manufacturer's instructions. For serpin B 13 specific staining sections were incubated with polyclonal antibody diluted at 0.5 μg/ml in Antibody-Diluent (Dako S2022) overnight at 4° C. Slides were washed with TBS+TWEEN 20 (LabVision 1666789) (3×2 min) and then incubated with the biotinylated secondary antibody (1 drop in 5 ml of PBS+1% horse serum) (Vectastain ABC kit, Elite Universal, Vector PK6200) for 30 min at room temperature. After washing with TBS+TWEEN 20 (3×2 min) sections were incubated with ABC reagent (1 drop Reagent A plus 1 drop Reagent B in 5 ml PBS) for 30 min at room temperature. Slides were washed with TBS+TWEEN 20 (2×2 min) and finally reacted with diaminobenzidine chromogen solution (DAB plus, Dako K3467) for 5 min, after rinsing with distilled water they were counterstained with hematoxylin and mounted. Rabbit IgG fraction (Dako X0903) was used as negative control.

Figure 2:
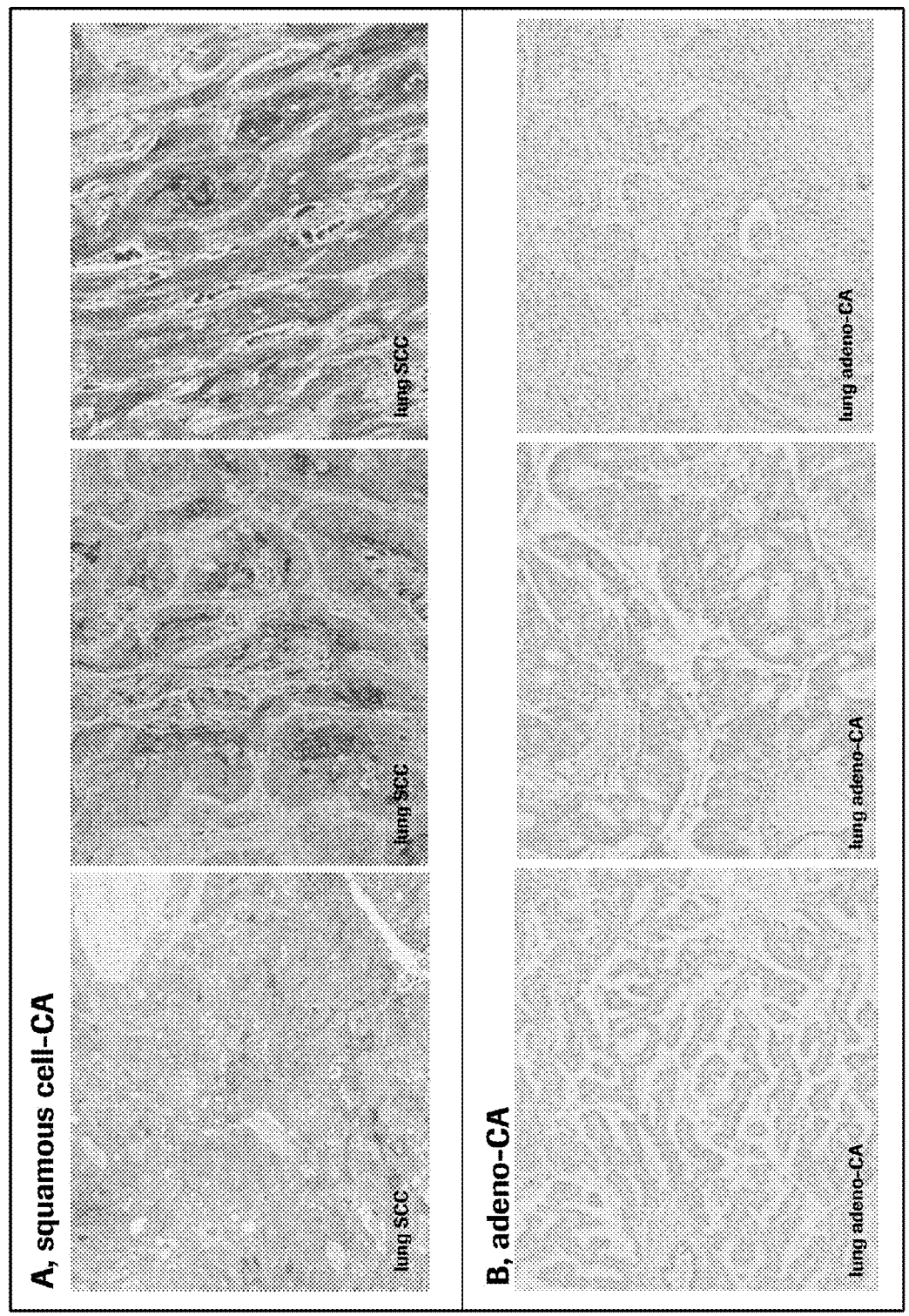
FIG. 2 Tissue sections from lung cancer patients classified as having SCC were compared with those derived from lung cancer patients classified as having Adeno-Ca of the lung. Shown are the results for tissue sections from 3 different SCC patients (panel A) and 3 different Adeno-Ca patients (panel B), respectively. Strong serpin B 13-specific staining is observed in all SCC samples, while there is no staining visible in the Adeno-Ca sections. Normal lung tissue (e.g., adjacent to tumor tissue in SCC) is negative for serpin B 13.

Tissue sections from SCC were compared with those derived from Adeno-Ca. Exemplarily, FIG. 2 shows the results for sections from 3 different SCC patients (panel A) and 3 Adeno-Ca patients (panel B), respectively. Serpin B 13-specific staining is observed in all SCC samples, while there is no staining with Adeno-Ca sections. Thus, specific expression of serpin B 13 in SCC tumor tissue is clearly confirmed by IHC analyses.

What is claimed is:

1. An in vitro method for assessing squamous cell lung carcinoma in a subject comprising
   measuring serpin B 13 protein in a sample from the subject and
   using the measurement obtained to assess squamous cell lung carcinoma, wherein the sample comprises a lung cell and a positive measurement for serpin B 13 protein is indicative for squamous cell lung carcinoma.

2. The method according to claim 1, wherein the sample is a piece of tissue obtained by biopsy.

3. The method according to claim 2, wherein the sample is a tissue section.

4. The method according to claim 1, wherein the sample is bronchoalveolar lavage or extracellular lining fluid.

5. The method according to claim 2, wherein the sample is mounted on a microscope slide.

6. The method according to claim 5, wherein the sample has been formalin fixed and paraffin embedded.

7. The method according to claim 1, wherein the sample is suspected or known to contain neoplastic cells.

8. The method according to claim 1, wherein serpin B 13 protein measurement is by an immunostaining method.

9. The method according to claim 1, wherein the sample is treated to release serpin B 13 protein and wherein serpin B 13 protein measurement is by an immunoassay procedure.

10. The method according to claim 9, wherein the immunoassay procedure is an ELISA or a western blot procedure.

11. An in vitro method for assessing squamous cell lung carcinoma in a subject comprising
measuring serpin B 13 protein in a sample from the subject, measuring serpin B 13 protein in a control sample, wherein the samples comprise a lung cell, and
comparing the measurements obtained to assess squamous cell lung carcinoma, wherein an elevated level of serpin B protein in the subject sample compared to the measurement in the control sample is indicative for squamous cell lung carcinoma.

12. The method according to claim 11, wherein the sample from the subject is a piece of tissue obtained by biopsy.

13. The method according to claim 12, wherein the sample from the subject is a tissue section.

14. The method according to claim 11, wherein the sample from the subject is bronchoalveolar lavage or extracellular lining fluid.

15. The method according to claim 12, wherein the sample from the subject is mounted on a microscope slide.

16. The method according to claim 15, wherein the sample from the subject has been formalin fixed and paraffin embedded.

17. The method according to claim 11, wherein the sample from the subject is suspected or known to contain neoplastic cells.

18. The method according to claim 11, wherein serpin B 13 protein measurement is by an immunostaining method.

19. The method according to claim 11, wherein the sample from the subject is treated to release serpin B 13 protein and wherein serpin B 13 protein measurement is by an immunoassay procedure.

20. The method according to claim 19, wherein the immunoassay procedure is an ELISA or a western blot procedure.

21. An in vitro method for differentially diagnosing squamous cell lung carcinoma in a subject compared to other non-small cell lung carcinoma (NSCLC), the method comprising
measuring serpin B 13 protein in a sample from the subject wherein the sample comprises non-small cell lung carcinoma cells and
using the measurement obtained to differentially diagnose squamous cell lung carcinoma compared to other NSCLC, wherein a positive measurement for serpin B 13 protein is indicative for squamous cell lung carcinoma and a negative measurement for serpin B 13 protein is indicative for other NSCLC.

22. The method according to claim 21, wherein the sample is a piece of tissue obtained by biopsy.

23. The method according to claim 22, wherein the sample is a tissue section.

24. The method according to claim 21, wherein the sample is bronchoalveolar lavage or extracellular lining fluid.

25. The method according to claim 22, wherein the sample is mounted on a microscope slide.

26. The method according to claim 25, wherein the sample has been formalin fixed and paraffin embedded.

27. The method according to claim 21, wherein the sample is suspected or known to contain neoplastic cells.

28. The method according to claim 21, wherein serpin B 13 protein measurement is by an immunostaining method.

29. The method according to claim 21, wherein the sample is treated to release serpin B 13 protein and wherein serpin B 13 protein measurement is by an immunoassay procedure.

30. The method according to claim 29, wherein the immunoassay procedure is an ELISA or a western blot procedure.

31. An in vitro method for managing treatment of a lung cancer patient comprising:
a) differentially diagnosing squamous cell lung carcinoma in the patient compared to other non-small cell lung carcinoma (NSCLC) by: measuring serpin B 13 protein in a sample from the subject wherein the sample comprises non-small cell lung carcinoma cells and using the measurement obtained to differentially diagnose squamous cell lung carcinoma compared to other NSCLC, wherein a positive measurement for serpin B 13 protein is indicative for squamous cell lung carcinoma and a negative measurement for serpin B 13 protein is indicative for other NSCLC; and
b) managing the treatment by initiating treatment for squamous cell lung carcinoma or a different NSCLC in accordance with the result obtained in step a).

* * * * *

SEQUENCE LISTING

```
<160> NUMBER OF SEQ ID NOS: 5

<210> SEQ ID NO 1
<211> LENGTH: 391
<212> TYPE: PRT
<213> ORGANISM: Homo sapiens

<400> SEQUENCE: 1

Met Asp Ser Leu Gly Ala Val Ser Thr Arg Leu Gly Phe Asp Leu Phe
1               5                   10                  15

Lys Glu Leu Lys Lys Thr Asn Asp Gly Asn Ile Phe Phe Ser Pro Val
            20                  25                  30

Gly Ile Leu Thr Ala Ile Gly Met Val Leu Leu Gly Thr Arg Gly Ala
        35                  40                  45

Thr Ala Ser Gln Leu Glu Glu Val Phe His Ser Glu Lys Glu Thr Lys
    50                  55                  60

Ser Ser Arg Ile Lys Ala Glu Glu Lys Glu Val Ile Glu Asn Thr Glu
65                  70                  75                  80

Ala Val His Gln Gln Phe Gln Lys Phe Leu Thr Glu Ile Ser Lys Leu
                85                  90                  95

Thr Asn Asp Tyr Glu Leu Asn Ile Thr Asn Arg Leu Phe Gly Glu Lys
            100                 105                 110

Thr Tyr Leu Phe Leu Gln Lys Tyr Leu Asp Tyr Val Glu Lys Tyr Tyr
        115                 120                 125

His Ala Ser Leu Glu Pro Val Asp Phe Val Asn Ala Ala Asp Glu Ser
    130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Thr Lys Leu Val
            165                 170                 175

Leu Val Asn Met Val Tyr Phe Lys Gly Gln Trp Asp Arg Glu Phe Lys
            180                 185                 190

Lys Glu Asn Thr Lys Glu Glu Lys Phe Trp Met Asn Lys Ser Thr Ser
        195                 200                 205

Lys Ser Val Gln Met Met Thr Gln Ser His Ser Ser Phe Thr Phe
    210                 215                 220

Leu Glu Asp Leu Gln Ala Lys Ile Leu Gly Ile Pro Tyr Lys Asn Asn
225                 230                 235                 240
```

-continued

```
Asp Leu Ser Met Phe Val Leu Pro Asn Asp Ile Asp Gly Leu Glu
                245                 250                 255

Lys Ile Ile Asp Lys Ile Ser Pro Glu Lys Leu Val Glu Trp Thr Ser
            260                 265                 270

Pro Gly His Met Glu Glu Arg Lys Val Asn Leu His Leu Pro Arg Phe
        275                 280                 285

Glu Val Glu Asp Gly Tyr Asp Leu Glu Ala Val Leu Ala Ala Met Gly
    290                 295                 300

Met Gly Asp Ala Phe Ser Glu His Lys Ala Asp Tyr Ser Gly Met Ser
305                 310                 315                 320

Ser Gly Ser Gly Leu Tyr Ala Gln Lys Phe Leu His Ser Ser Phe Val
                325                 330                 335

Ala Val Thr Glu Glu Gly Thr Glu Ala Ala Ala Thr Gly Ile Gly
            340                 345                 350

Phe Thr Val Thr Ser Ala Pro Gly His Glu Asn Val His Cys Asn His
        355                 360                 365

Pro Phe Leu Phe Phe Ile Arg His Asn Glu Ser Asn Ser Ile Leu Phe
    370                 375                 380

Phe Gly Arg Phe Ser Ser Pro
385                 390

<210> SEQ ID NO 2
<211> LENGTH: 339
<212> TYPE: PRT
<213> ORGANISM: Homo sapiens

<400> SEQUENCE: 2

Met Asp Ser Leu Gly Ala Val Ser Thr Arg Leu Gly Phe Asp Leu Phe
1               5                   10                  15

Lys Glu Leu Lys Lys Thr Asn Asp Gly Asn Ile Phe Phe Ser Pro Val
            20                  25                  30

Gly Ile Leu Thr Ala Ile Gly Met Val Leu Leu Gly Thr Arg Gly Ala
        35                  40                  45

Thr Ala Ser Gln Leu Glu Glu Val Phe His Ser Glu Lys Glu Thr Lys
    50                  55                  60

Ser Ser Arg Ile Lys Ala Glu Lys Glu Val Ile Glu Asn Thr Glu
65                  70                  75                  80

Ala Val His Gln Gln Phe Gln Lys Phe Leu Thr Glu Ile Ser Lys Leu
                85                  90                  95

Thr Asn Asp Tyr Glu Leu Asn Ile Thr Asn Arg Leu Phe Gly Glu Lys
            100                 105                 110

Thr Tyr Leu Phe Leu Gln Lys Tyr Leu Asp Tyr Val Glu Lys Tyr Tyr
        115                 120                 125

His Ala Ser Leu Glu Pro Val Asp Phe Val Asn Ala Ala Asp Glu Ser
    130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Thr Lys Leu Val
                165                 170                 175

Leu Val Asn Met Val Tyr Phe Lys Gly Gln Trp Asp Arg Glu Phe Lys
            180                 185                 190

Lys Glu Asn Thr Lys Glu Glu Lys Phe Trp Met Asn Lys Ile Ile Asp
        195                 200                 205

Lys Ile Ser Pro Glu Lys Leu Val Glu Trp Thr Ser Pro Gly His Met
    210                 215                 220
```

```
Glu Glu Arg Lys Val Asn Leu His Leu Pro Arg Phe Glu Val Glu Asp
225                 230                 235                 240

Gly Tyr Asp Leu Glu Ala Val Leu Ala Ala Met Gly Met Gly Asp Ala
            245                 250                 255

Phe Ser Glu His Lys Ala Asp Tyr Ser Gly Met Ser Ser Gly Ser Gly
            260                 265                 270

Leu Tyr Ala Gln Lys Phe Leu His Ser Ser Phe Val Ala Val Thr Glu
            275                 280                 285

Glu Gly Thr Glu Ala Ala Ala Thr Gly Ile Gly Phe Thr Val Thr
        290                 295                 300

Ser Ala Pro Gly His Glu Asn Val His Cys Asn His Pro Phe Leu Phe
305                 310                 315                 320

Phe Ile Arg His Asn Glu Ser Asn Ser Ile Leu Phe Phe Gly Arg Phe
                325                 330                 335

Ser Ser Pro

<210> SEQ ID NO 3
<211> LENGTH: 98
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgcgaattc attaaagagg agaaattaac tatgagagga tcgcatcacc atcaccatca    60
cattgaaggc cgtgattcac ttggcgccgt cagcactc                           98

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcataagctt tcattaagga gaagaaaatc tgccgaagaa g                       41

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Arg Gly Ser His His His His His His Ile Glu Gly Arg
1               5                   10
```